United States Patent [19]
Herweck et al.

[11] Patent Number: 5,320,100
[45] Date of Patent: Jun. 14, 1994

[54] IMPLANTABLE PROSTHETIC DEVICE HAVING INTEGRAL PATENCY DIAGNOSTIC INDICIA

[75] Inventors: Steve A. Herweck, Nashua; Theodore Karwoski, Hollis; Paul Martakos, Pelham, all of N.H.

[73] Assignee: Atrium Medical Corporation, Hollis, N.H.

[21] Appl. No.: 29,982

[22] Filed: Mar. 12, 1993

Related U.S. Application Data

[63] Continuation of Ser. No. 760,728, Sep. 16, 1991, abandoned.

[51] Int. Cl.⁵ .................. A61B 6/00; A61B 19/00; A61F 2/06; A61F 2/02
[52] U.S. Cl. ..................... 128/654; 128/899; 623/1; 623/11; 623/12
[58] Field of Search ............. 623/1, 11, 12; 128/654, 128/899

[56] References Cited

U.S. PATENT DOCUMENTS

| | | | |
|---|---|---|---|
| 4,041,931 | 8/1977 | Elliott et al. | 623/1 X |
| 4,202,349 | 5/1980 | Jones | 623/1 X |
| 4,219,520 | 8/1980 | Kline | 623/1 X |
| 4,254,180 | 3/1981 | Kune | 623/1 X |
| 4,416,028 | 11/1983 | Ericksson et al. | 623/1 |
| 4,562,596 | 1/1986 | Kornberg | 623/1 |
| 4,647,416 | 3/1987 | Seiler, Jr. et al. | 623/1 X |
| 4,713,075 | 12/1987 | Kurland | 623/13 |
| 4,731,073 | 3/1988 | Robinson | 623/1 |
| 4,787,391 | 11/1988 | Elefteriades | 128/654 |
| 4,790,313 | 12/1988 | Borrelly | 623/12 X |
| 5,024,232 | 6/1991 | Smid et al. | 623/1 X |
| 5,047,050 | 9/1991 | Arpesawi | 623/1 |
| 5,061,281 | 10/1991 | Mares et al. | 623/11 |

FOREIGN PATENT DOCUMENTS

| | | | |
|---|---|---|---|
| 3323430 | 1/1985 | Fed. Rep. of Germany | 623/12 |
| 8500511 | 2/1985 | World Int. Prop. O. | 623/13 |
| 8806026 | 8/1988 | World Int. Prop. O. | 623/1 |
| 8806871 | 9/1988 | World Int. Prop. O. | 623/12 |

*Primary Examiner*—David Isabella
*Assistant Examiner*—Dinh X. Nguyen
*Attorney, Agent, or Firm*—Lahive & Cockfield

[57] ABSTRACT

An implantable prosthetic device comprises a remotely detectible component disposed in the body forming the device for allowing the device to be detected by x-ray, ultrasonic, or MRI imaging. By disposing at least two remotely detectible components in the body of the device, the effective flow diameter provided by the device can be monitored. A method for monitoring a patient having a damaged or dysfunctional vascular pathway includes the steps of implanting in the patient the disclosed prosthetic device and monitoring the patency of the device by x-ray, ultrasonic, MRI, or other form of remote imaging.

22 Claims, 1 Drawing Sheet

IMPLANTABLE PROSTHETIC DEVICE HAVING INTEGRAL PATENCY DIAGNOSTIC INDICIA

This application is a continuation of application Ser. No. 760,728 filed Sep. 16, 1991, now abandoned.

BACKGROUND OF THE INVENTION

One type of implantable device is a synthetic vascular graft such as is commonly used to replace damaged or dysfunctional arterial or venous pathways, for example at the site of an aneurysm or occlusion. Bypass grafts are often used to divert blood flow around damaged regions to restore blood flow. Another use of vascular prostheses is for creating a bypass shunt between an artery and vein, specifically for multiple needle access, such as is required for hemodialysis treatments. Following multiple percutaneous invasions into a vein, the vein may either collapse along the puncture track or become aneurysmal, leaky or fill with clot, causing significant risk of pulmonary embolization. Vascular prostheses have been used for many years as an alternative to patients' own veins for vascular access during hemodialysis.

Materials research has led to the development of some synthetic materials for use in artificial vascular prostheses. For example, polytetrafluoroethylene (PTFE), a polymeric material which may be stretched to a specific length and expanded to a specific thickness, is often used to fabricate single lumen artificial veins and arteries. Typically, however, PTFE vascular grafts cannot safely be used to withdraw blood until they have been in place in the body for a minimum of 14 days after surgery and have become surrounded by fibrotic tissue. This is because bleeding occurs at the site of a needle puncture in PTFE grafts if fibrotic tissue is absent. Complications which can result from early puncturing of PTFE arteriovenous fistulas include a hematoma surrounding the graft, false aneurysm, and graft occlusion.

Various other synthetic materials, in addition to PTFE, have been used for vascular grafts, including Dacron ® brand and other synthetic polyester fibers, mandrel spun polyurethane, and silicon elastomer fibers. Additionally, vascular grafts have been formed using autologous saphenous vein, modified bovine carotid xenograft, and modified human umbilical vein. None, however, has overcome the problems associated with early failure of the graft following implantation.

A problem associated with known vascular grafts stems from their delicate structure making them difficult to handle and position properly during surgery. Due to their circumferentially uniform appearance, the grafts may be twisted during implantation, which can reduce the openness, or patency, of the implanted graft.

Another problem associated with known vascular grafts is that they are transparent to known non-surgical techniques for viewing that are generally used to detect structures in the body. These techniques include x-rays, MRI scanning, fluoroscopy, ultrasound, and nuclear magnetic resonance. As a result, post-implantation examination of known vascular grafts is difficult. If a surgeon suspects that a blockage of an implanted vascular graft has occurred, for example, she must inject radiopaque dye into the patient through the graft. The dye allows the graft to be visible during fluoroscopic examination to determine whether it has collapsed or is satisfactorily transporting blood flow. This process is invasive to the patient and places further burdens on the patient's circulatory system.

Various marking devices have been developed to avoid the need for injecting dye into a patient who has undergone vascular graft implantation. U.S. Pat. No. 4,202,349 (Jones, May 13, 1980), for example, discloses a radiopaque blood vessel marker for attachment to the side wall of a blood vessel or vascular graft. The marker is a substantially flattened disk which is sutured into place by the surgeon. The Jones vessel markers are not well suited for use with PTFE vascular prostheses because it is difficult to elicit natural occlusion of suture holes in PTFE due to the relative elasticity of the porous PTFE tubing materials.

U.S. Pat. No. 4,787,391 (Elefteriades Nov. 29, 1988) discloses a device for the marking the anastomosis, or joining site, of a coronary graft so that the anastomosis can be localized fluoroscopically after surgery. The device includes gold indicators which are arranged on a hemostatic material which is absorbed or dissolved completely in the body during the healing period, leaving the gold markers at the site. This device is useful for marking the area of the anastomosis, but does not allow the vascular graft itself to be viewed during fluoroscopic examination.

It is, therefore, an object of the present invention to provide a vascular graft having integral diagnostic indicia for determining the patency (openness) of the graft vessel by non-invasive techniques. It is also an object of the present invention to provide a vascular graft having integral radiopaque or MRI markers that do not need to be sutured to the graft. It is still another object of the present invention to provide a method for treating a patient having a damaged or dysfunctional arterial or venous pathway using the detectible vascular grafts of the present invention.

SUMMARY OF THE INVENTION

These and other objects are achieved by the present invention which features an implantable prosthetic device, such as a vascular graft, having integral diagnostic indicia for determining the position and/or the patency or openness of the graft. The device comprises a biocompatible tubular body defining at least two lumina. A primary lumen is designated for blood flow, and at least one secondary lumen has a remotely detectible material, such as a radiopaque component or material different in density from the body, which is disposed within it. All of the lumina extend along the article's longitudinal axis. The remotely detectible component allows the position of the graft and/or the openness of the graft to be determined by non-invasive means. For example, fluoroscopy can be utilized in the case of a radiopaque material being disposed in a secondary lumen. On the other hand, MRI or ultrasonic examination can detect a material different in density from the body.

The detectible component can be, for example, a radiopaque material, such as a barium compound, which is injected into one of the secondary lumina after extrusion of the body. In another embodiment, the detectible component is a metallic strip of radiopaque material, such as tantalum, which is threaded through one of the secondary lumina. In the case of the remotely detectible component being a material having a different density from that of the body, it can either be injected into the secondary lumen after extrusion of the body or co-extruded with the body.

As stated, the detectible component can be formed integrally with the article or inserted after extrusion of the article into a secondary lumen. Additionally, the component can extend either substantially along the entire length of the body, coextensive with the primary lumen, or along only a portion thereof. In a particularly advantageous embodiment of the invention, two detectible components are provided and disposed substantially diametrically opposedly in relation to the central, primary, lumen so that the effective flow diameter of the primary lumen can be determined by inspection of the graft.

A method for non-invasively monitoring a patient whose damaged or dysfunctional vascular pathway has been replaced with the present device is also the subject of the present invention. The method comprises implanting the inventive device in the patient under conditions sufficient to establish blood flow through the primary lumen. At least one secondary lumen contains remotely detectible material, such as radiopaque or MRI detectible material. The position and/or patency of the graft can thereby be ascertained by examining the patient using a non-invasive technique such as x-ray or fluoroscopic imaging, in the case of radiopaque materials, or MRI or ultrasonic scanning, in the case of differing density materials.

DETAILED DESCRIPTION OF THE INVENTION

Figure 1:
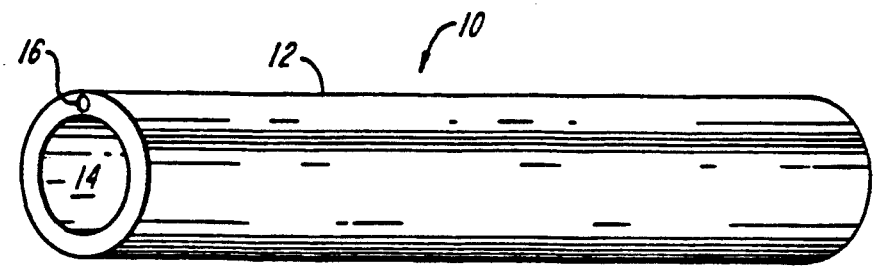
FIG. 1 is schematic illustration showing a perspective view of an implantable bilumenal vascular graft having a radiopaque material integrated in one of the lumina.

The present invention features a prosthetic device such as a vascular graft, which includes integral diagnostic indicia for detecting the position or patency of the graft by non-invasive external means. The device is formed from a biocompatible tubular structure which defines at least two lumina, a primary lumen which is adapted for blood flow and at least one secondary lumen within which a remotely detectible component is disposed. The device of the invention allows detection by x-ray, ultrasonic, MRI and/or other non-invasive types of imaging. This allows the position of the graft and/or the degree of patency to be determined.

The tube structures of the invention can be manufactured from any suitable biocompatible material that can be arranged to form a microporous structure. Polymeric materials which are useful for this purpose include, for example, either expanded or unexpanded polytetrafluoroethylene (PTFE), Dacron® brand polyester, and other synthetic polyester fibers such as mandrel spun polyurethane and silicone elastomeric fibers. Also, copolymeric materials such as described in U.S. Pat. Nos. 4,187,390 and 4,973,609 can be utilized. These are materials made up of more than one type of monomer and have advantages as described in the cited patents, in some applications. The structures can also be formed by extrusion, form molding, or weaving using techniques well known in the art.

In a preferred embodiment, the inventive prosthesis is manufactured by paste forming and rapidly stretching and/or expanding highly crystalline, unsintered, polytetrafluoroethylene. Paste forming by extrusion of PTFE is well-known in the art. Generally, the steps in paste-forming include mixing the resin with a lubricant, such as odorless mineral spirits, and then forming the resin by extrusion into shaped articles. The lubricant is removed from the extruded article by drying, following which the article is sintered by its being heated above its crystalline melting point of approximately 327° C. The sintered, unexpanded, article is a relatively impermeable product. To achieve a greater degree of permeability in the finished product, however, the prostheses of the invention can be further treated prior to sintering.

Paste-formed, dried, unsintered, shapes can be further treated by expanding and/or stretching them in one or more directions under certain conditions so that they become porous yet retain their strength. Such stretching and expansion with increased strength occurs with certain preferred tetrafluoroethylene resins, e.g., PTFE. The porosity of the material is affected by the temperature and rate at which it is stretched and expanded. A method for manufacturing porous PTFE tubing appropriate for use in the present invention is described in detail, for example, in U.S. Pat. No. 3,953,566, and U.S. Pat. No. 4,973,609 the teachings of both of which are hereby incorporated by reference herein.

Stretched and expanded PTFE is characterized by a microstructure of nodes interconnected by small fibrils. The space between the nodes and the number of fibrils is controlled by changes in the temperature and rate of stretching and expansion of the PTFE, to produce tubing having predetermined porosity and flex qualities. For example, products which are stretched and expanded at high temperatures and high rates have a more homogeneous structure, i.e., they have smaller, more closely spaced nodes, which nodes are interconnected with a greater number of fibrils. While the resulting structure is stronger than products stretched and expanded at lower temperatures and rates, the porosity is also reduced. Thus, by controlling these two factors, it is possible to construct a series of tube structures having a range of porosity within a desirable range of strength.

When tube structures manufactured from PTFE as described above are heated to above the lowest crystalline melting point of the PTFE, disorder begins to occur in the geometric structure of the crystallites and the crystallinity decreases. This is accompanied by a concomitant increase in the amorphous content of the polymer. Amorphous regions within the crystalline structure greatly inhibit slippage along the crystalline axis of the crystallite and lock fibrils and crystallites so that they resist slippage under stress thereby resulting in a higher strength product. Heat treatment may be considered to be, therefore, an amorphous locking process, which results in an increase in the amorphous content and the strength of the structure. Heat treatment above 327° C. has been found to cause a two-fold increase in the strength of PTFE tubular structures.

Since the upper melting range of PTFE is approximately 345° C., heat treatment above this temperature is even more effective to increase the strength of the structure. Similar results can be achieved at lower temperatures if exposure time is accordingly increased. In one embodiment of the invention, the optimum heat treating temperature is in the range of from about 350° C. to about 370° C., with heating periods in the range of from about 5 seconds to about 1 hour. Other factors which affect the strength of the polymer matrix include the strength of the extruded material before expansion, the degree of crystallinity of the polymer, the rate and temperature at which the expansion is performed, and degree of amorphous locking.

The tube structures can be formed using other paste-forming operations known to those skilled in the art, such as, for example, any of the available molding or weaving processes. Paste-forming resins other than PTFE may also be used which are generally formable into such tube structures, and which result in relatively fluid impermeable structures. Due to the physiological properties of the arteriovascular system it is important that the tube structures be gas permeable, or selectively gas permeable, to permit oxygen-carbon dioxide exchange. However, even gas impermeable tube structures may be useful as vascular grafts in certain AV regions.

In a preferred embodiment the tube structures of the present invention are formed by extrusion of PTFE. Extrusion is performed using dies of predetermined shape of the type known in the art. The dies may also be manufactured from materials available and well known in the art.

After the PTFE resin is formed, such as by extrusion as discussed above, it is stretched and/or expanded and then sintered while being held in the stretched and/or expanded state. Stretching refers to elongation of formed resin while expansion refers to enlargement of the formed resin perpendicularly to its longitudinal axis. The rate of stretching and the stretch ratio affect the porosity of the finished product in a predictable manner allowing a prosthetic device to be produced having a specified porosity. The rate of stretching refers to the percentage of elongation per second that the resin is stretched while the stretch ratio refers to the relationship between the final length of the stretched resin and the initial length of the stretched resin. For example, stretching an extruded PTFE tube at a stretch ratio of two to one and a stretch rate of sixty results in a porosity of approximately forty. This porosity is unitless and is determined as set forth on page eighty-four of the American Society For Testing of Materials' Special Technical Publication Number 898. So, for example, based on stretch ratios ranging from two to one, to six to one, a stretch rate of sixty percent per second yields a porosity of between approximately forty and approximately ninety, a stretch rate of one hundred and forty percent per second yields a porosity of between approximately sixty and approximately eighty-five, and a stretch rate of nine hundred percent per second yields a porosity of between approximately sixty-five and approximately eighty-five.

In addition to the porosity, the geometry of the node and fibril network of PTFE can be controlled during stretching and expansion. In the case of uniaxial stretching, that is, elongation of the formed PTFE resin along the direction of extrusion, the nodes are elongated causing the longer axis of each node to be oriented perpendicularly to the direction of stretch. Accordingly, the fibrils are oriented parallel to the direction of stretch. Biaxial stretching, additionally includes expanding the PTFE resin in the radial direction and can be utilized to produce a prosthetic device having a composite porosity. As in uniaxial stretching, the rate and ratio of radial expansion affects the resulting porosity of the prosthetic device.

Various remotely detectible materials which are generally known in the art are suitable for disposition in the secondary lumen. For example, radiopaque materials which are useful in the present invention include barium sulfate and tantalum wire. Also, barium filled elastomers, such as are used for surgical sponges are suitable. Essentially, any biologically inert metal-containing compound can be used. Additionally, the secondary lumen can be filled with a material having a different density from that of the article itself which will enable detection by ultrasonic and MRI techniques.

One embodiment of the present device is shown in FIG. 1. An implantable vascular graft 10 is formed of a tubular body 12 which defines a lumen 14. Disposed in the perimeter of the article 12 is a remotely detectible component 16 such as those discussed above.

Figure 2:
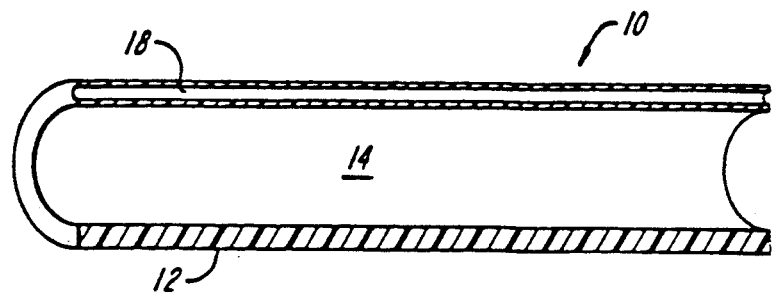
FIG. 2 is schematic illustration showing a perspective cutaway view of the vascular graft shown in FIG. 1 showing both lumina without the radiopaque material.

FIG. 2 shows a cross-section of the vascular graft shown in FIG. 1, with the detectible component 16 removed. The FIGURE shows an additional lumen 18. The detectible component 16 is disposed in lumen 18. The detectible component 16 can occupy the entire lumen 18 or merely a portion thereof depending upon the requirements of the specific application.

Figure 3:
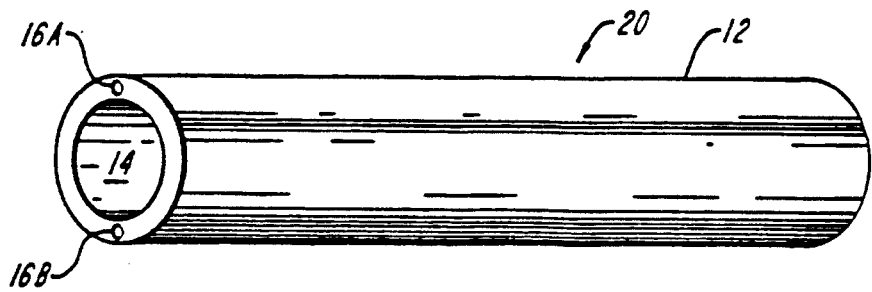
FIG. 3 is schematic illustration showing a perspective view of a triluminal vascular graft of the present invention in which the two small lumina both contain a radiopaque material.

FIG. 3 shows another embodiment of the present invention wherein an implantable vascular graft 20 includes detectible components 16A and 16B disposed in the graft's body 12. In this manner, by imaging after implantation, the effective flow diameter of the graft 20 can be determined since it is clearly related to the distance between the detectible component 16A and the detectible component 16. In this embodiment of the invention, in addition to the flow-providing lumen 14, the body 12 defines two lumina for accommodating the detectible components 16A and 16B.

Figure 4:
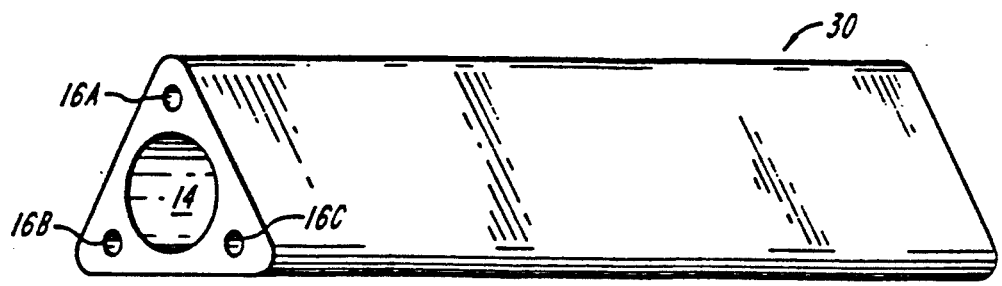
FIG. 4 is schematic illustration showing a perspective view of a quadriluminal embodiment of the vascular graft of the present invention in which the three small lumina all contain a radiopaque material.

Still another embodiment of the invention, shown in FIG. 4, includes an implantable vascular graft 30 having a body 12 which defines a flow-providing lumen 14 and in which are disposed three detectible components 16A, 16B and 16C. Still other embodiments of the invention will be readily apparent to those ordinarily skilled in the art.

The method of the invention is practiced by implanting in a patient a vascular graft as described above to promote flow through a damaged or dysfunctional pathway. In this method, the graft is implanted in a patient such that blood flow is established through the primary lumen of the device. The secondary lumina contain the detectible material. By then examining the graft by x-ray, MRI, or other form of imaging, depending upon the type of material disposed in the secondary lumen, the position, and effective flow diameter of the graft can be determined.

For example, in the case of a graft having a single line of detectible material co-extensive with the graft, the surgeon can follow the line of the graft, e.g., to ascertain whether the graft has become twisted, looped or otherwise not properly positioned during the surgery. In another embodiment, a graft having two or more secondary lumina which are filled with detectible material is implanted. The doctor can then monitor blood flow through the graft by observing through x-ray or MRI imaging, the movement of the detectible lines relative to each other. For example, a fluoroscopic examination by a physician would reveal pulsation of the graft vessel as the detectible lines would constantly move in and out with respect to one another; whereas if blood flow is stopped, no movement will be observed. By using detectible lines which are co-extensive with the graft, the openness of the graft along its entire length can be observed. Another advantage to the present invention is that the detectible material is an integral part of the graft, therefore, it cannot become separated or dissociated from the graft after implantation. The present method of monitoring an implanted vascular graft is, therefore, more reliable than traditional methods involving the suturing of radiopaque markers to a vein, artery, or graft.

Those skilled in the art will recognize or be able to ascertain, using no more than routine experimentation, many equivalents to the specific materials and components described herein. Such equivalents are intended to be encompassed in the scope of the following claims.

What is claimed is:

1. An implantable prosthetic device for connection to a fluid flow pathway of a patient, the device comprising:
   a biocompatible microporous wall that surrounds an interior space which constitutes a lumen that extends along a longitudinal axis and is adapted for accommodating fluid flow therethrough, and
   plural remotely detectable components formed integrally within secondary lumina in said wall to move therewith said secondary lumens formed by extrusion and each extending in a line parallel to said longitudinal axis, such that said plural remotely detectable components are remotely detectable as liens that move relative to each other with pulsatile motion of the wall as blood flows through the lumen for indicating patency of the lumen.

2. A device as set forth in claim 1, wherein said remotely detectable components are formed of a material comprising a radiopaque polymer.

3. A device as set forth in claim 1, wherein said remotely detectable components comprise metallic strips.

4. A device as set forth in claim 1, wherein said remotely detectable components are formed of a material which has a density different from that of said tubular body.

5. A device as set forth in claim 1, wherein said wall consists of polytetrafluoroethylene.

6. A device as set forth in claim 5, wherein said polytetrafluoroethylene is selected from the group consisting of stretched polytetrafluoroethylene, expanded polytetrafluoroethylene, and stretched and expanded polytetrafluoroethylene.

7. A device as set forth in claim 1, wherein said wall consists of a material including copolymers.

8. A device as set forth in claim 1, wherein said remotely detectable components are arranged substantially equidistant about the circumference of said lumen.

9. A device according to claim 1, wherein the secondary lumina include at least two lumina with a length coextensive with the primary lumen, forming remotely detectable lines that indicate openness at all portions along the primary lumen.

10. A device according to claim 8, wherein the secondary lumina include at least two lumina with a length coextensive with the primary lumen, forming remotely detectable lines that indicate openness at all portions along the primary lumen.

11. An implantable prosthetic device comprising a biocompatible microporous tubular body defining
   a primary lumen enclosed by said body and adapted for accommodating fluid flow therethrough, and
   at least two secondary lumina formed integrally extending by extrusing with said body in respective lines parallel to the primary lumen and arranged equidistant about said primary lumen, and a remotely detectable material disposed in each of said secondary lumina for forming remotely detectable lines that move relative to each other as the body moves for visibly indicating patency of the primary lumen.

12. A device as set forth in claim 11, wherein said remotely detectible material is a radiopaque polymer.

13. A device as set forth in claim 11, wherein said remotely detectible material is a metallic strip.

14. A device as set forth in claim 11, wherein said remotely detectible material has a density different from that of said tubular body.

15. A device as set forth in claim 11, wherein said tubular body consists of polytetrafluoroethylene.

16. A device as set forth in claim 15, wherein said polytetrafluoroethylene is selected from the group consisting of stretched polytetrafluoroethylene, expanded polytetrafluoroethylene, and stretched and expanded polytetrafluoroethylene.

17. A device as set forth in claim 11, wherein said tubular body consist of a material including a copolymer.

18. A device according to claim 11, wherein the secondary lumina include at least two lumina with a length coextensive with the primary lumen, forming remotely detectable lines that indicate openness at all portions along the primary lumen.

19. A method for monitoring the position of patency of a vascular graft in a patient, the method comprising the steps of
   a. providing a vascular graft comprising a biocompatible microporous tubular body defining a primary lumen extending along an axis and at least two secondary lumina formed integrally each extending with said body in a line parallel to said axis and containing remotely detectable material, the secondary lumina moving relative to each other with motion of the body,
   b. implanting the vascular graft in the patent under conditions sufficient to establish blood flow through the primary lumen, and
   c. monitoring the graft by a remote imaging technique to image the remotely detectable material as lines, motion of the lies indicating patency of the primary lumen.

20. A method as set forth in claim 19, wherein said remote imaging technique is selected form the group consisting of x-ray imaging, ultrasonic imaging and magnetic resonance imaging.

21. A method as set forth in claim 19, wherein the step of monitoring the vascular graft is carried out substantially simultaneously with the step of implanting the vascular graft.

22. A method as set forth in claim 19, wherein the step of monitoring the vascular graft is carried out after the step of implanting the vascular graft.

* * * * *

UNITED STATES PATENT AND TRADEMARK OFFICE
CERTIFICATE OF CORRECTION

PATENT NO. : 5,320,100
DATED : June 14, 1994
INVENTOR(S) : Steve A. Herweck, Theodore Karwoski, and Paul Martakos It is certified that error appears in the above-indentified patent and that said Letters Patent is hereby corrected as shown below:

Column 7, line 35 replace "liens" with --lines--.

Column 8, lines 7-8 replace "extending by extrusing" with --by extrusion-- and after "with said body" insert --extending--

Column 8, line 49, replace "patent" with --patient--.

Column 8, line 57, replace "selected form" with --selected from--.

Signed and Sealed this

Thirtieth Day of January, 1996

BRUCE LEHMAN

Attest:

Attesting Officer

Commissioner of Patents and Trademarks